US011566618B2

United States Patent
Gabriel et al.

(10) Patent No.: US 11,566,618 B2
(45) Date of Patent: Jan. 31, 2023

(54) ROTARY PUMP DRIVEN MEDICAMENT DELIVERY DEVICE

(71) Applicant: MEDICO INVEST AG, St. Gallen (CH)

(72) Inventors: Jochen Gabriel, Stuttgart (DE); Herbert Bechtold, Denkingen (DE)

(73) Assignee: MEDICO INVEST AG

( * ) Notice: Subject to any disclaimer, the term of this patent is extended or adjusted under 35 U.S.C. 154(b) by 38 days.

(21) Appl. No.: 16/104,058

(22) Filed: Aug. 16, 2018

(65) Prior Publication Data

US 2019/0085843 A1 Mar. 21, 2019

Related U.S. Application Data

(60) Provisional application No. 62/561,036, filed on Sep. 20, 2017.

(51) Int. Cl.
*F04C 2/22* (2006.01)
*F04C 13/00* (2006.01)
(Continued)

(52) U.S. Cl.
CPC ........... *F04C 2/22* (2013.01); *A61M 5/14212* (2013.01); *F04C 13/001* (2013.01); *F04C 14/20* (2013.01);
(Continued)

(58) Field of Classification Search
CPC .......... F04C 2/22; F04C 13/001; F04C 14/20; F04C 15/0015; F04C 15/008;
(Continued)

(56) References Cited

U.S. PATENT DOCUMENTS 3,318,515 A * 5/1967 Jones ...................... F02B 77/02
418/61.2
4,018,548 A * 4/1977 Berkowitz ............ F01C 21/106
418/61.2
(Continued)

FOREIGN PATENT DOCUMENTS

AT 376885 B 1/1985
CN 1076249 A2 9/1993
(Continued)

OTHER PUBLICATIONS

Invitation to pay fees and partial international search report of the international searching authority dated Nov. 7, 2018 of corresponding international patent application PCT/EP2018/074537.
(Continued)

*Primary Examiner* — Alexander B Comley
(74) *Attorney, Agent, or Firm* — Quarles & Brady LLP (57) ABSTRACT

A rotary pump is presented for use in a medicament delivery device, where the pump has a back plate having an inner surface and a rotor housing is positioned adjacent to the back plate having a peripheral wall. A front plate support is connected to the back plate and a flexible front plate is positioned between the front plate support and the rotor housing. The pump is rotated using a planetary gear transmission, where an eccentric shaft is operatively connected to the planetary gear mechanism. A rotor is rotationally fixed to the eccentric shaft and movably positioned within the rotor housing. The rotor has three lobes, where each lobe has two peripheral curved surfaces sharing a common apex, where a first portion of each peripheral surface adjacent to the apex defines a non-smooth curve.

11 Claims, 10 Drawing Sheets

(51) Int. Cl.
*F04C 15/00* (2006.01)
*A61M 5/142* (2006.01)
*F04C 14/20* (2006.01)

(52) U.S. Cl.
CPC ........ *F04C 15/008* (2013.01); *F04C 15/0015* (2013.01); *F04C 15/0065* (2013.01); *F04C 2240/20* (2013.01); *F04C 2240/30* (2013.01); *F04C 2240/40* (2013.01); *F04C 2240/60* (2013.01); *F04C 2270/185* (2013.01); *F05C 2203/06* (2013.01); *F05C 2251/02* (2013.01)

(58) Field of Classification Search
CPC .. F04C 15/0065; F04C 18/22; F04C 2240/20; F04C 2240/40; F04C 2240/60; F04C 2240/30; A61M 5/14212
USPC ........................................ 417/410.3; 418/61.2
See application file for complete search history.

(56) References Cited

U.S. PATENT DOCUMENTS

| | | | | |
|---|---|---|---|---|
| 4,137,024 | A | * | 1/1979 | Jones .................. F01C 1/22 418/116 |
| 4,551,073 | A | | 11/1985 | Schwab |
| 6,520,754 | B2 | * | 2/2003 | Randolphi .............. F04C 18/22 417/410.3 |
| 2009/0060728 | A1 | | 3/2009 | Grimes et al. |
| 2011/0126794 | A1 | | 6/2011 | Higashi et al. |
| 2017/0072132 | A1 | | 7/2017 | Nystrom |
| 2019/0085843 | A1 | * | 3/2019 | Gabriel .................. F04C 2/22 |

FOREIGN PATENT DOCUMENTS

| | | | |
|---|---|---|---|
| DE | 4425429 | A1 | 1/1996 |
| EP | 2322760 | A1 | 5/2011 |
| JP | S4970013 | A | 7/1974 |
| JP | S53125313 | U | 10/1978 |
| JP | S56147387 | * | 11/1981 |
| JP | S56147387 | U | 11/1981 |
| JP | S6217322 | A | 1/1987 |
| JP | S6217322 | A * | 1/1987 |
| JP | 2002130150 | A | 5/2002 |
| JP | 201309990 | A | 10/2013 |
| JP | 2013209990 | A | 10/2013 |

OTHER PUBLICATIONS

International Search Report and Written Opinion for PCT/EP2018/074537 dated Aug. 6, 2019.
Chinese Office Action dated Mar. 1, 2022 in corresponding Chinese Patent Application No. 201880060918.1 (with English Translation).
Chinese Search Report dated Jul. 2, 2021 in corresponding Chinese Patent Application No. 201880060918.1 (with English Translation).
International Preliminary Report on Patentability and Written Opinion dated Mar. 24, 2020 in corresponding International Patent Application No. PCT/EP2018/074537.

* cited by examiner

ROTARY PUMP DRIVEN MEDICAMENT DELIVERY DEVICE

CROSS REFERENCE TO RELATED APPLICATION

This application claims priority of U.S. provisional patent application No. 62/561,036, filed Sep. 20, 2017, the entire content of which is incorporated herein by reference.

TECHNICAL AREA

The present disclosure relates to a rotary pump and to a medical device for the administration of one or more liquid medicaments to a patient that uses the rotary pump mechanism to supply the medicament via a needle or other conduit. The rotary pump delivers accurate volumetric flow of medicament using a uniquely designed rotor that prevents unwanted or unexpected transfer of medicament from one chamber to another.

BACKGROUND

The use of rotary type pumps based on the original Wankel combustion engine design are known, but are not in wide spread commercial use. US Pub. 2017/0072132, for example, discloses a medical injection system employing a rotary pump having a bi-lobe rotor and U.S. Pat. No. 4,551,073 discloses a trochoidal rotor piston for use in a rotary pump for pumping blood during clinical procedures. Of the known type of rotary pumps used generally in the medical field, all use either a standard Wankel three-lobe rotor design or a two-lobe design. Characteristic of these rotor designs is that the surface of each lobe of the piston rotor is defined by two continuous smooth shaped edges terminating at an apex of the lobe. In some cases, flexible seals are positioned at the apex to improve the sealing capabilities. Because the smooth curve shaped edges of the rotor do not correspond well with the inner peripheral wall of the rotor housing gaps occur between chambers that cause unwanted transfer of medicament from the desired chamber to an empty chamber. This unwanted transfer then reduces the expected volume that is ultimately expelled from the chamber. This loss of volume, or lower than expected amount expelled, is detrimental to dose accuracy when using such a pump to deliver medicaments to a patient in an infusion and/or bolus injection procedure.

Accordingly, there is a strong need to develop a rotary pump design that eliminates or significantly diminishes the amount of unwanted transfer of medicament from one chamber to another such that a medicament can be accurately delivered to a patient.

The present disclosure, as presented below, solves the above-mentioned problems with existing and known rotary pump designs and provides a pump rotor design that fulfills the needs and requirements of delivering accurate volumetric flow of medicament to a patient.

BRIEF DESCRIPTION

In one possible embodiment, the medicament delivery device is driven by a rotary pump having a back plate having an inner surface, where a rotor housing is positioned adjacent to the back plate and has a peripheral wall. A front plate support is connected to the back plate and a flexible front plate is positioned between the front plate support and the rotor housing.

The pump is rotated using a planetary gear transmission, where an eccentric shaft is operatively connected to the planetary gear mechanism. A rotor is rotationally fixed to the eccentric shaft and movably positioned within a rotor housing. The rotor has three lobes, where each lobe has two peripheral curved surfaces sharing a common apex, where a first portion of each peripheral surface adjacent to the apex defines a non-smooth curve.

The peripheral wall defines a bilobar rotor housing with a trochoidal shaped wall and has at least a first and second lobe. Depending on the position of the rotor, especially the apexes, relative to the trochoidal wall, the bilobar pump chamber can have four separate chambers. The planetary gear transmission preferably has a stationary timing pinion positioned on the back plate and a ring gear integral with the rotor, where the ring gear has teeth that mesh with cooperating teeth on the timing pinion such that the ring gear rotates eccentrically around the timing pinion.

Figure 4:
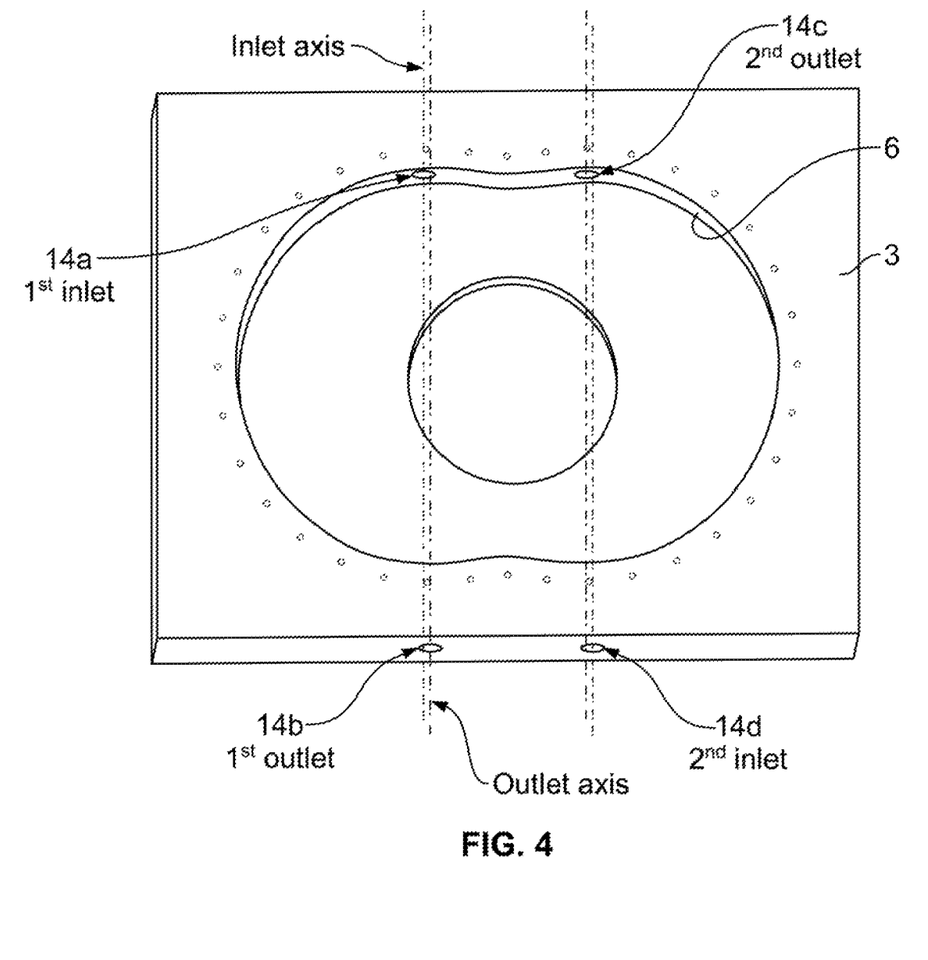
FIG. 4 is a cut away view of the rotor housing of the present disclosure showing two inlets and two outlets where the longitudinal axes of the inlets are offset from the longitudinal axes of the outlets.

Each of the peripheral curved surfaces of the lobes preferably terminates at a midpoint located equidistant between two apexes and where a second portion of the peripheral curved surface is located between the first portion and the midpoint and defines a smooth curve. The rotor housing preferably has an inlet port and a discharge port, each having a center point and a longitudinal axis, where the inlet port center point is offset from the center point of the discharge port. This offset preferably is of a sufficient distance such that the rotor cannot open both the inlet port and outlet port at the same time. In some cases, the longitudinal axes of the inlet and outlet are parallel to each other. In such a situation the longitudinal axes are offset a distance sufficient such that the rotor cannot open both the inlet port and outlet port at the same time. Such a configuration is illustrated in FIG. 4.

An eccentric is preferably connected directly to an end of an eccentric drive shaft, which itself is journaled to a bearing positioned in the rear plate. The eccentric allows the rotor to be connected to the eccentric drive shaft so that it is rotationally fixed to the eccentric drive shaft. It is preferred that the rotor is fabricated from a flexible material such that the apexes do not require separate sealing members. In a most preferred assembly the flexible material is silicone. It is also advantageous if the front plate support comprises both open areas and solid support areas.

As stated, the rotor housing is bilobar having a first lobe and a second lobe, where each lobe preferably has an inlet bore hole in fluid communication with an inlet port and an outlet bore hole in fluid communication with a discharge port. In some instances it is desirable that each port has a longitudinal axis, where the inlet ports are positioned such that the longitudinal axes are parallel to and offset from the longitudinal axes of the discharge ports. One possible embodiment of the present disclosure is a pump having a back plate with an inner surface and a rotor housing positioned adjacent to the back plate and having a peripheral wall. A front plate support is connected to the back plate and a flexible front plate is positioned between the front plate support and the rotor housing.

The pump also includes a planetary gear transmission that is connected to an eccentric shaft, which can be driven by a motor means. The planetary gear transmission can have a stationary timing pinion positioned on the back plate and a ring gear integral with the rotor, where the ring gear has teeth that mesh with cooperating teeth on the timing pinion such that the ring gear rotates eccentrically around the timing pinion.

A rotor is rotationally fixed to the eccentric shaft and movably positioned within rotor housing, the rotor comprising three lobes, where each lobe has two peripheral curved surfaces sharing a common apex, where a first portion of each peripheral surface adjacent to the apex defines a non-smooth curve. Each of the peripheral curved surfaces can terminate at a midpoint located equidistant between two apexes and can include a second portion of the peripheral curved surface that is located between the first portion and the midpoint and defines a smooth curve. Preferably, the rotor is fabricated of a flexible material such that the apexes do not require separate sealing members. One such flexible material is silicone.

The peripheral wall defines a pump chamber with a trochoidal wall and can have a first and second chamber. The rotor housing can include an inlet port and a discharge port, each having a longitudinal axis, where the inlet port longitudinal axis is parallel to and offset from the longitudinal axis of the discharge port. This offset of the longitudinal axes is preferably of a sufficient distance such that the rotor cannot open both the inlet port and outlet port at the same time.

Another possible embodiment of the present disclosure is a medicament delivery device for delivering a measured quantity of liquid medicament from a reservoir to an end point, such as, a patient through a catheter or to an injection site. The medicament delivery device has a housing with an inlet connected to the reservoir of medicament through a conduit and an outlet connected to a discharge device, where the housing has a back plate having an inner surface. A rotor housing is positioned adjacent to the back plate and a rotor is rotationally fixed to an eccentric shaft and movably positioned within the rotor housing. Preferably, the rotor has three lobes, where each lobe has two peripheral curved surfaces sharing a common apex, where a first portion of each peripheral surface adjacent to the apex defines a non-smooth curve. A drive means, preferably an electric motor, is connected to the eccentric shaft to rotate the eccentric shaft during medicament delivery, where medicament is drawn into a chamber from the reservoir in the rotor housing through the inlet as the rotor turns relative to the rotor housing and the medicament is expelled through the outlet and into the discharge device.

These and other aspects of, and advantages with, the present disclosures will become apparent from the following detailed description of the present disclosure and from the accompanying drawings.

BRIEF DESCRIPTION OF DRAWINGS

In the following detailed description of the present disclosure, reference will be made to the accompanying drawings, of which

DETAILED DESCRIPTION

Figure 1:
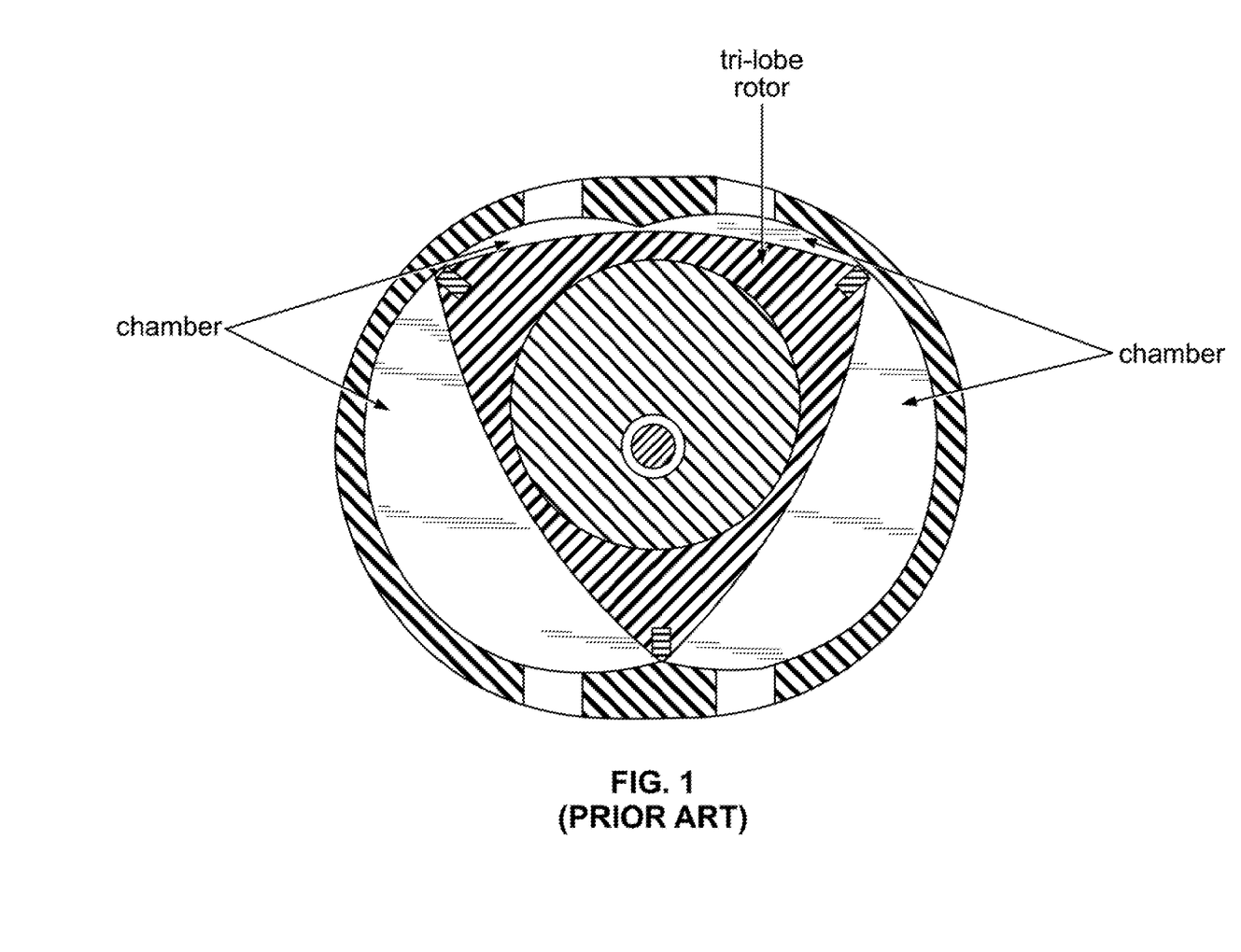
FIG. 1 shows a conventional Wankel rotor design known to the art and as depicted in U.S. Pat. No. 4,551,073.

The conventional or known Wankel type rotary pump design (see FIG. 1) has not been used for the accurate and precise delivery of a medicament to a patient. This is likely because the known design inherently cannot repeatedly deliver an accurate dose of medicament, which is extremely important in all injection or pump type medical devices. The rotary pump design of the present disclosure 1 uses a tri-lobe rotor 2 within a bilobar chamber 16 that differs from the conventional Wankel type rotor in that each of the three lobes 2a, 2b, & 2c (or sides) contains two separate sections (see FIG. 3A). This is in contradistinction to the conventional Wankel design that only has a single continuous curved section per side of the rotor (see FIG. 3B). The rotor 2 of the present disclosure further has pairs of two peripheral curved surfaces 20 sharing a common apex 22, where a first portion of each peripheral surface 21 adjacent to the apex defines a non-smooth curve.

Figure 5:
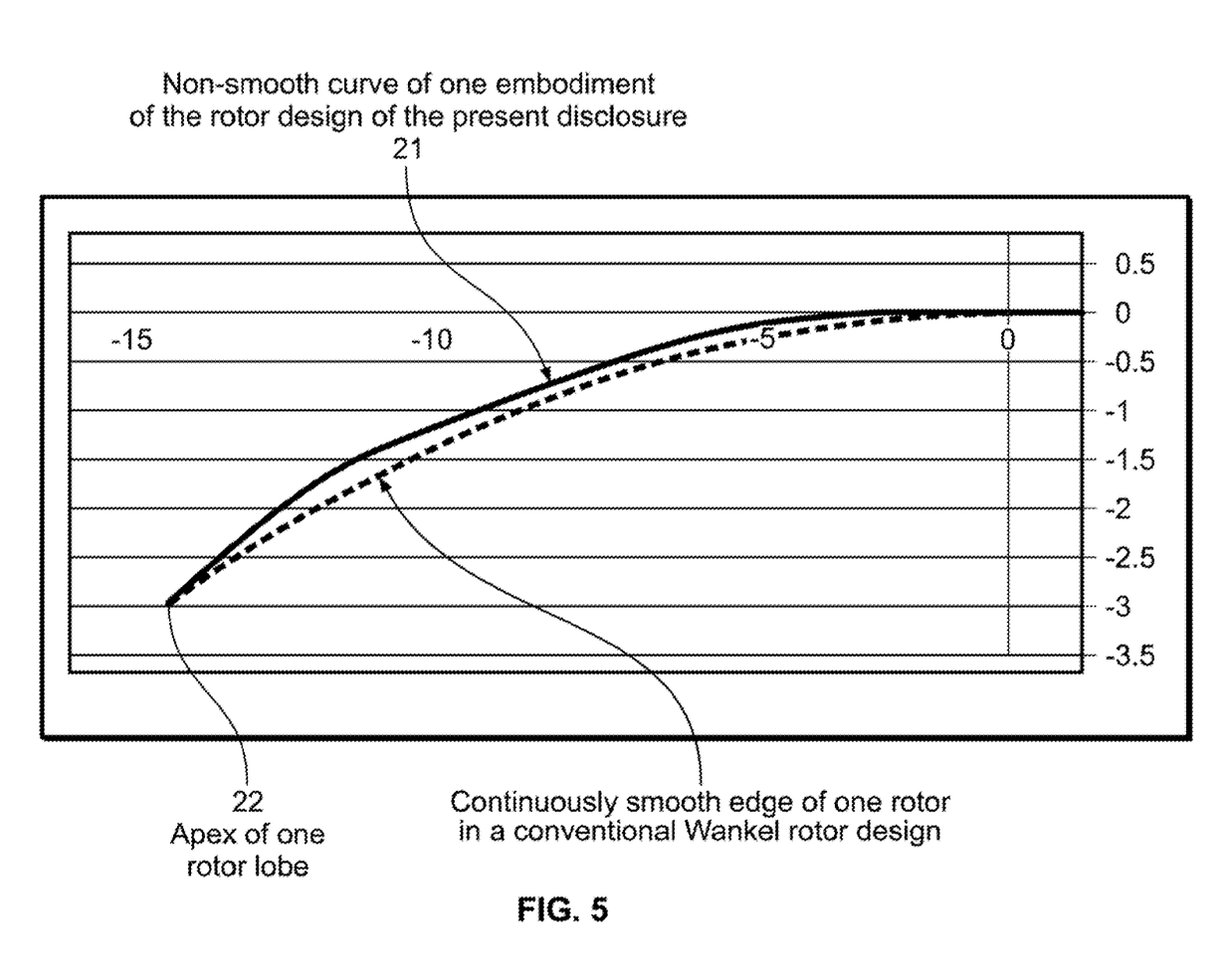
FIG. 5 is a graphical representation showing the curvature of a portion of one lobe of the rotor of the present disclosure compared to a known Wankel type rotor.
Figure 7A:
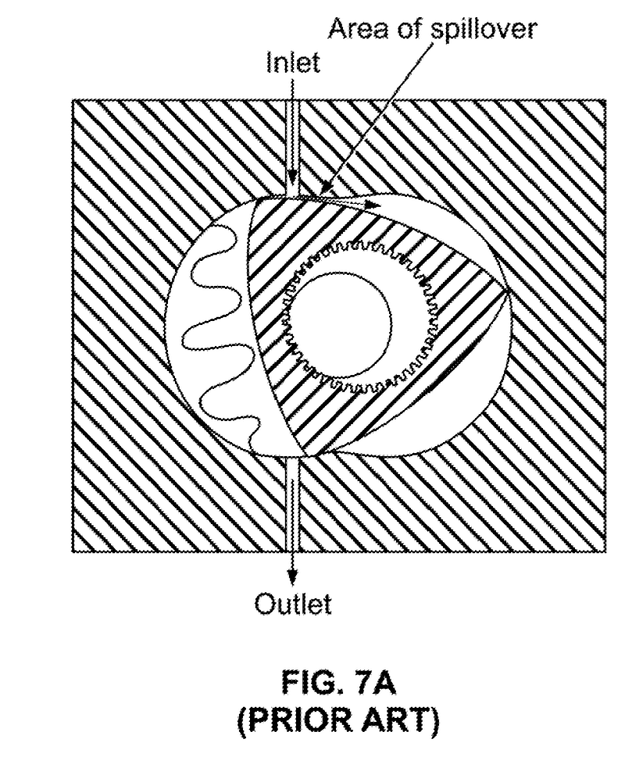
FIGS. 7A and 7B graphically illustrate the issue of unwanted transfer of medicament from one chamber to another in the known Wankel type pumps (FIG. 7A) and no such transfer using a rotor design of the present disclosure.
Figure 7B:
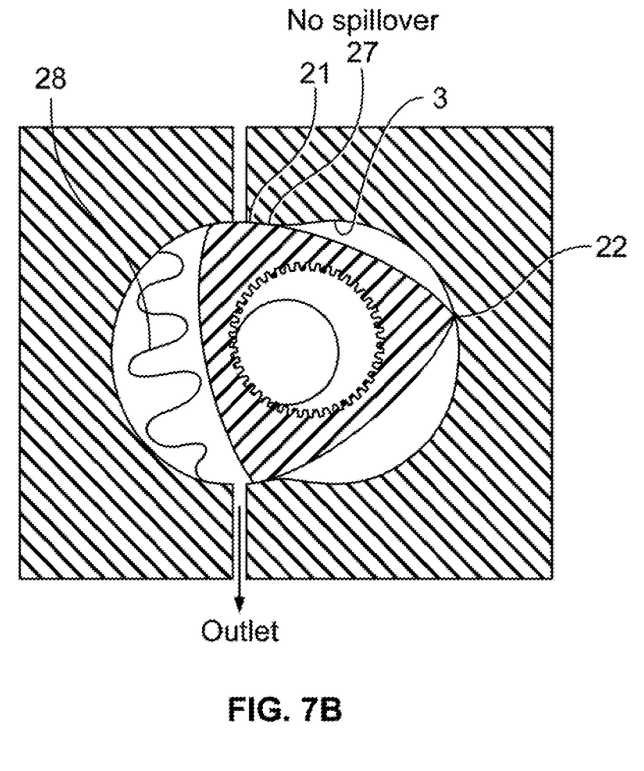

A comparison of the smooth curve of the conventional Wankel design compared to the present disclosure is illustrated in FIG. 5. The non-smooth curve 21 of the present disclosure ensures sealing between the outer rotor surface 26 and the peripheral wall 6 of the rotor housing 3. This sealing prevents the unwanted transfer of fluid, e.g., medicament, from one chamber to another, which has a detrimental effect on dose accuracy. This unwanted transfer, i.e., area of spillover, is illustrated in FIG. 7A for the known Wankel rotor design. FIG. 7B illustrates that the non-smooth curve portion 21 of the present disclosure creates a tight seal of the rotor 2 with the rotor housing 3, which prevents the deleterious transfer of fluid 28. From these figures it is evident that the difference between the known Wankel geometry and the rotary pump design of the present disclosure is not directed to the sealing between the apexes of the rotor lobes and the peripheral wall of the rotor housing, but instead is the sealing between the rotor sections that terminate at the apexes.

Figure 2:
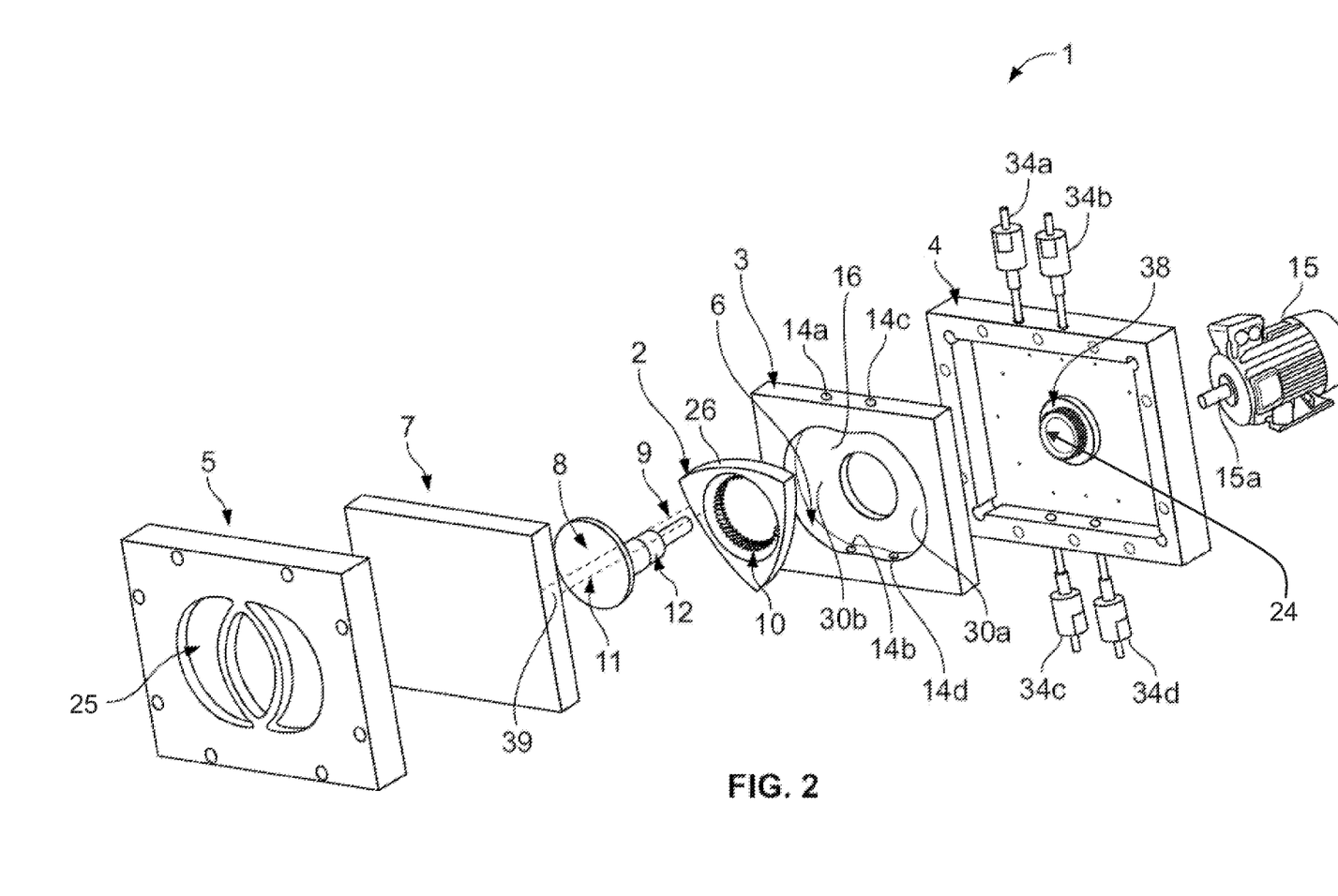
FIG. 2 is an exploded perspective view of one embodiment of the rotary pump of the present disclosure.
Figure 6A:
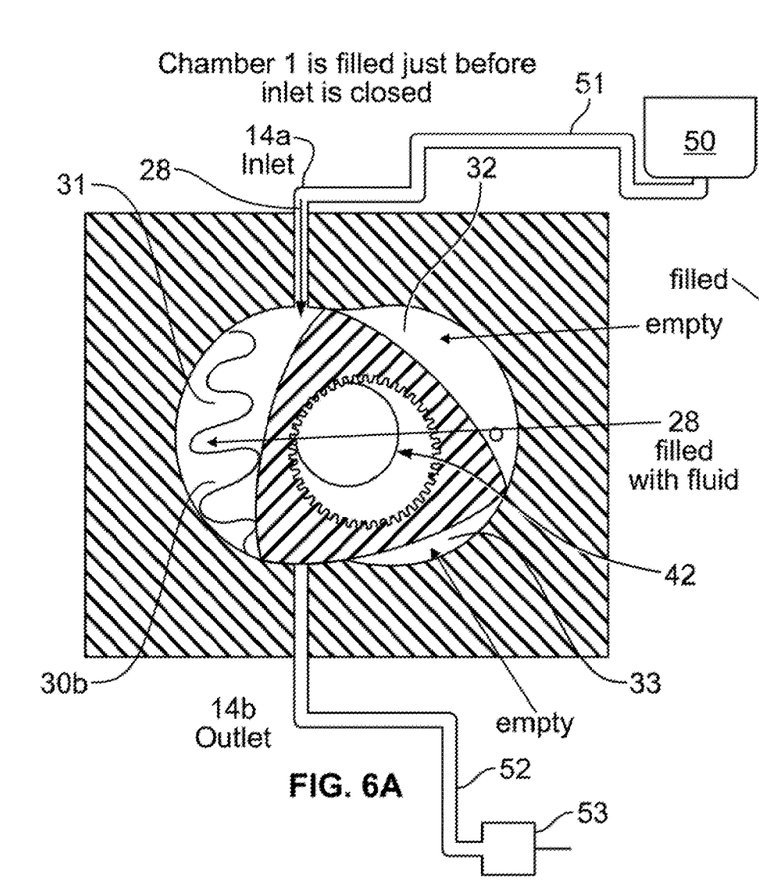
FIGS. 6A through 6E graphically represent the filling and discharge of the chambers within an embodiment of the rotary pump of this disclosure.
Figure 6B:
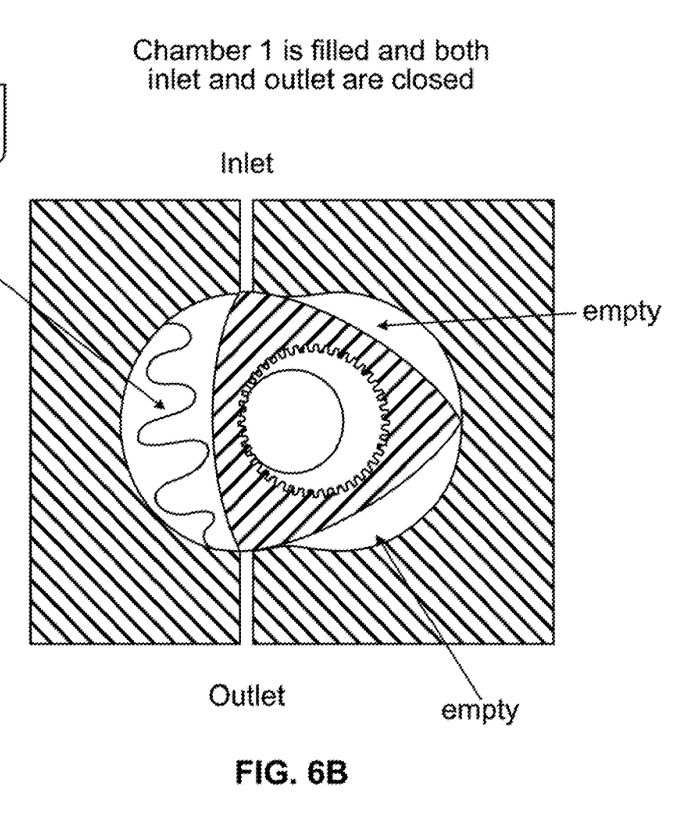
Figure 6C:
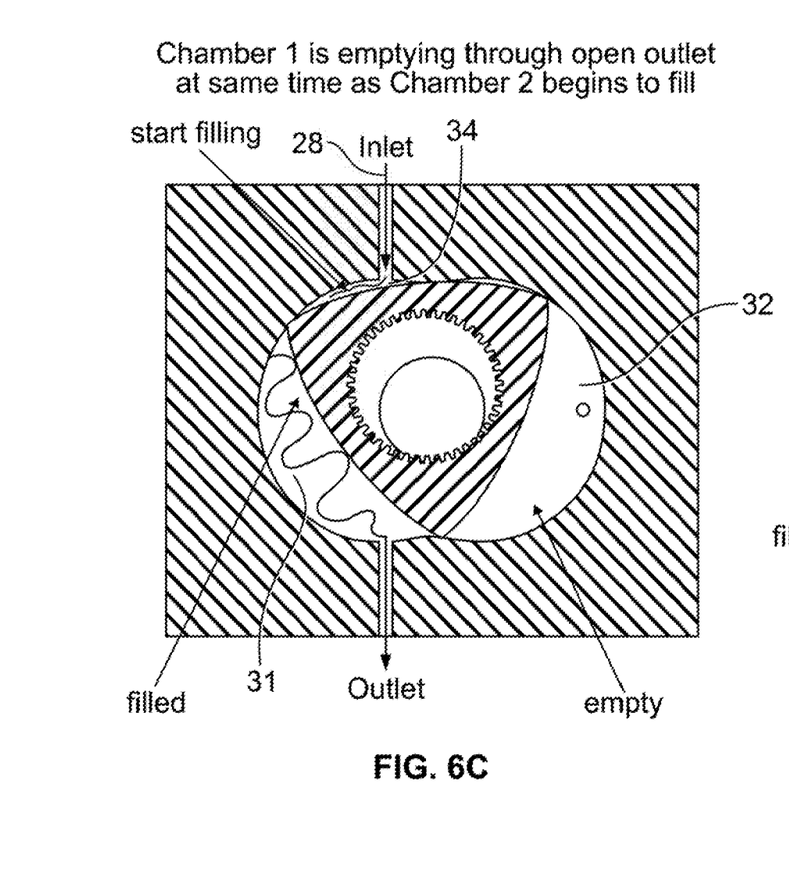
Figure 6D:
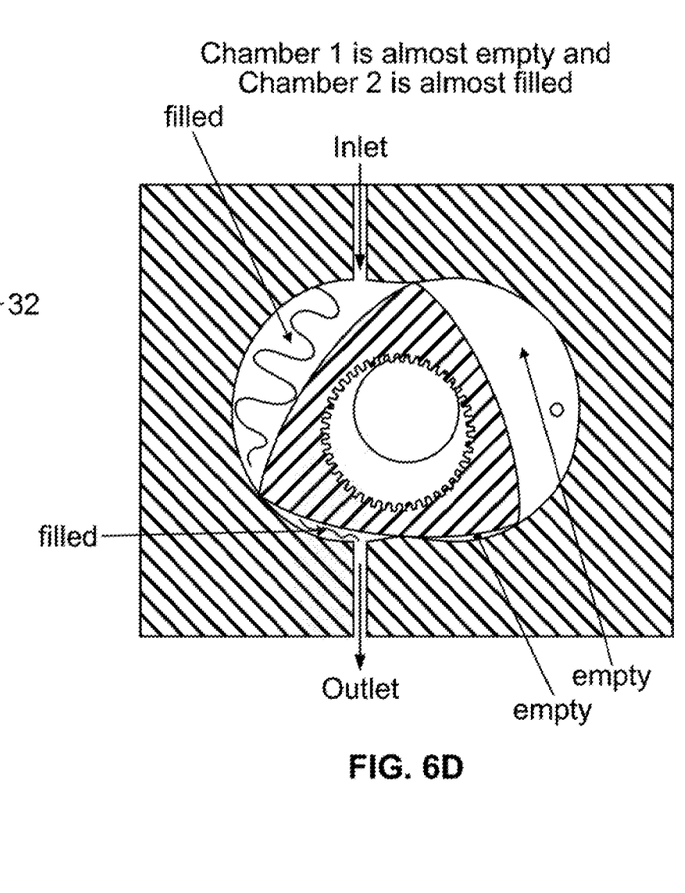
Figure 6E:
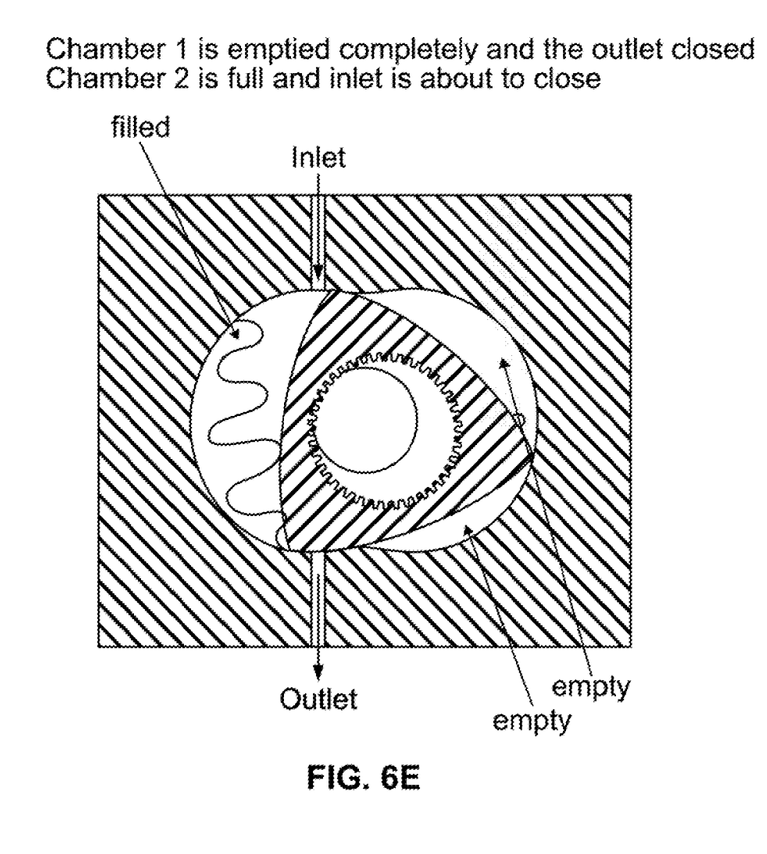

FIG. 2 shows an exploded view of at least one possible embodiment of the rotary pump design of the present disclosure. In this design, the rotor housing 3 is bilobar, i.e., has two lobes 30a, 30b, each lobe having an inlet port 14a, 14d and an outlet port 14b, 14c. In some cases, it is desirable to use one set of the inlet/outlet ports to monitor the pump performance and not to actually move fluid into and out of the chambers 31, 32 defined by the position of the rotor within the one or the other housing lobes (see FIG. 6A). Stated differently, in some embodiments of the rotary pump there is only a single inlet 14a and a single outlet port 14b, both of which are associated with the same housing lobe 30b and both are used to move fluid (medicament) 28 in and out of the pump. In such an embodiment with one inlet and one outlet, a large empty chamber 32 occurs at certain times in the opposite housing lobe 30a. To compensate for the possibility of a vacuum forming in an empty chamber it may be desirable to have additional ports that can be used as pressure compensators. FIG. 6A shows one possible embodiment where a reservoir 50 containing multiple doses of medicament 28 is connected via conduit 51 to the inlet 14a of the rotary pump. The outlet 14b is connected via conduit 52 with a discharge device, for example, an injection needle, a catheter, nozzle, jet or similar component that can introduce a single dose, or bolus, or continuous flow of the medicament 28 to an injection site.

As mentioned, the rotor housing 3 can include a single set of inlet and outlet ports, preferably configured as bore holes 14a, 14b in the rotor housing wall 6. Conduit and/or fittings can be connected to these bore holes to form and define the inlet and outlet ports (see FIG. 4). In other embodiments, it is advantageous to have two sets of inlet and outlet ports. The inlet and outlet ports could also include check valves 34a, 34b, 34c, & 34d to insure proper flow direction and/or pressurization of the medicament through the rotary pump. For dose accuracy purposes, the bore holes must be located such that the rotor can completely close the inlet and not allow any leakage of medicament. Likewise, the outlet bore hole should be positioned relative to the rotor to ensure complete closure by the rotor outer surface. For these reasons, it preferred that the bore holes are located in the peripheral wall of the rotor housing. Known prior rotary pump designs require that both the inlet and outlet are open at the same time at least some of the time. The rotary pump of the present disclosure does not have this feature. Stated differently, the pump of the present disclosure never has both an inlet and an outlet open at the same time. Either the inlet is open or the outlet is open, but not both. This ensures that medicament fluid in a first chamber is expelled completely out of the outlet in fluid communication with that chamber and not carried over to a next or second chamber.

The configuration and shape of the peripheral wall 6 that defines the rotor housing 3 follows a traditional double lobe trochoid shape having smooth curves. Smooth curved walls in the rotor housing 3 allow a good liquid and pressure seal to be maintained between each of the three rotor apexes 22 as they rotate around and contact the peripheral housing wall. For this reason, it is not desirable to modify the peripheral wall of the rotor housing, e.g., making wall sections having non-smooth cures. Changing the peripheral wall design may result in leakage where the apexes could lose contact with the wall.

Figure 3A:
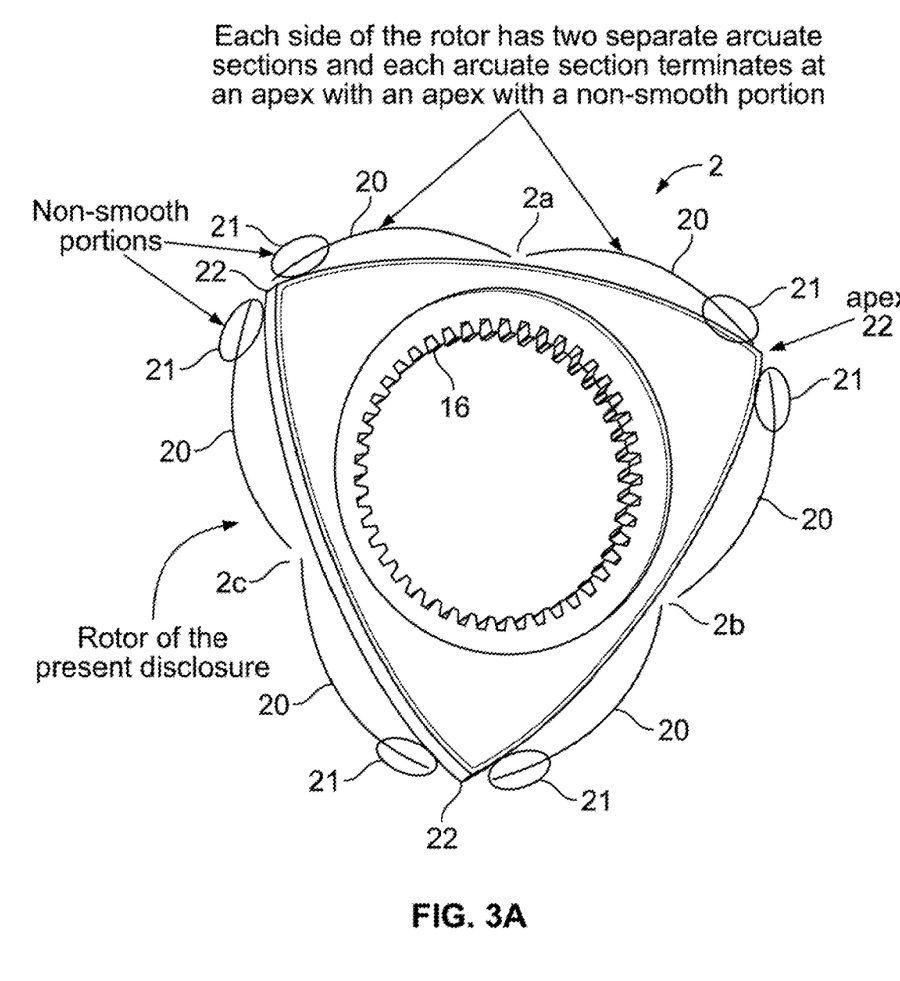
FIG. 3A shows an exaggerated schematic representation of a rotor design according to one embodiment of the present disclosure.
Figure 3B:
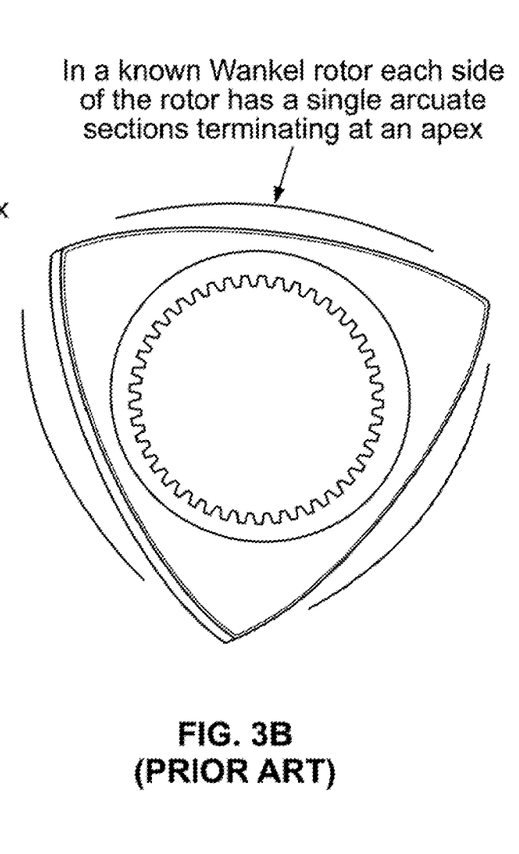
FIG. 3B shows an exaggerated schematic representation of a known rotor design.

FIG. 3A illustrates a preferred rotor 2 design that has two distinct arcuate sections 20 between each apex 22. This compares to the known Wankel type rotor that has only one arcuate section between each apex, as illustrated in FIG. 3B for comparison to FIG. 3A. The smooth curve of the known rotor design inherently causes the unwanted transfer of medicament between the chambers at certain rotor positions. As mentioned, this is detrimental to dose accuracy. The non-smooth curve of the present disclosure ensures that the chambers are always sealed off from each other. As such, each filling of a chamber is precise and with the same known volume of medicament, which is ultimately delivered to the patient. Preferably, there is one non-smooth geometry of the two peripheral curved surfaces that share a common apex that fits to a given geometry of the peripheral wall of the rotor housing.

The ratio of the diameters of the timing pinion 38 and ring gear 10 can vary, but have to match to the eccentricity and to the trochoid. Otherwise, the eccentric shaft 12 could not be turned to actuate the rotary pump 1 of the present disclosure. One possible ratio is 3:1. Another parameter that can be adjusted is the offset distance 39 of the shaft axis of rotation $S_c$ 11 to the eccentric axis of rotation $e_c$ 9 (see FIG. 2). Although the offset distance 39 is not a unique number it must be a distance that works with the ratio of diameters and to the trochoid.

The eccentric shaft 12 is driven and rotated by any known mechanical motor means. Preferably, an electric motor 15 having a rotatable connection can be used that connects with the eccentric shaft 12 on one side of the motor such that the eccentric shaft is rotated by the motor using a planetary gear transmission 42 that includes an eccentric 8, a ring gear 10, eccentric shaft 12 and timing pinion 38. The electric motor 15 which can be used, can be any conventional electric motor of the high-speed low torque type, namely, in alternating current or a direct current motor with or without brushes or commutators. The planetary gear transmission 42 transmits the rotational drive force of the motor to rotate the rotor 2 within the rotor housing 3. One example of this planetary gear transmission is shown in FIG. 2 where the eccentric shaft 12 is connected to an eccentric 8, which in turn is connected to the rotor 2. The motor shaft 15a is journaled to a bearing 24 positioned in the back plate 4. As the motor shaft 15a rotates, the connected eccentric shaft 12, the eccentric 8 and rotor 2 must also rotate. The ring gear 10 on the inside of the rotor 2 is engaged with a stationary pinion gear 38 attached to the back plate 4. As the rotor 2 is rotated the ring gear 10 moves around the pinion gear 38 and traces out the epicycloid shape, i.e., bilobar chamber 16, of the rotor housing 3.

The material of construction of the rotor 2 is preferably a flexible material so as to avoid the use of inserted seals in the rotor or the peripheral housing wall. Preferably the rotor is fabricated from one or more flexible materials or a combination of flexible and nonflexible materials. One preferred flexible material is silicone, however, other materials can be used in the manufacturing process, provided that the portions of the rotor that are in contact with the medicament fluid are biocompatible and have no deleterious effects on the medicament. In some cases, it may be desirable to fabricate the apexes 22 of the rotor with a material more flexible than the rest of the rotor to ensure that a tight seal is formed with the wall.

The material of construction of the flexible front plate 7, like the material of construction of the rotor must be selected so that it is compatible with the liquid medicament being pumped, i.e., the fabrication material cannot have a deleterious effect on the medicament. Preferably, the material of construction is chosen so the flexible front plate 7 can compensate for pressure differences by flexing and retracting as needed to maintain a constant internal operating pressure of the pump. The front plate support should be sufficiently rigid enough to hold the flexible parts together and ensure adequate sealing so that leakage does not occur. Sealing is important in order to maintain consistent and reproducible dose accuracy. In a preferred configuration the front plate support can have one or more open areas 25 (see FIG. 2) where the pressure compensation is needed. The solid parts of the front plate support 5 are positioned to ensure that the front plate 7 has stability in those locations.

Figure 8:
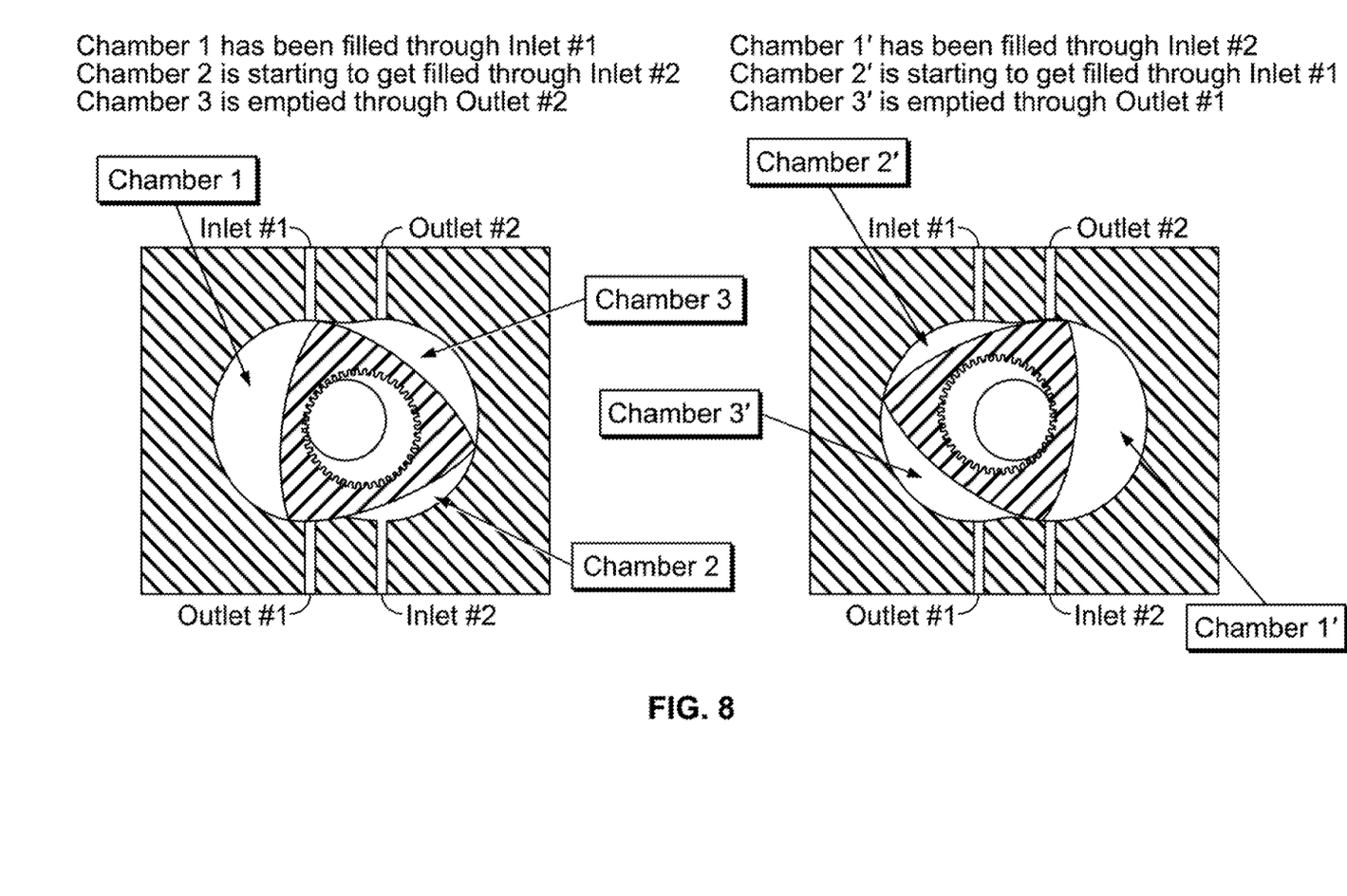
FIG. 8 shows another embodiment of the rotary pump of the present disclosure having two inlets and two outlets.

Operation of one possible embodiment of the rotary pump 1 of this disclosure is graphically illustrated in FIGS. 6A-6E. Operation of another possible rotary pump design is illustrated in FIG. 8.

It is to be understood that the embodiments described above and shown in the drawings are to be regarded only as non-limiting examples of the possible designs of the safety assembly and such designs may be modified in many ways.

We claim:

1. A medicament delivery device comprising:
a pump having an inlet connected to a reservoir of medicament and an outlet connected to a discharge device, the pump comprising:
a rotor housing having a peripheral wall, an inlet port, and a discharge port, wherein the peripheral wall defines a pump chamber with a trochoidal wall; and
a rotor movably positioned within the rotor housing, the rotor comprising three lobes and three respective apexes, wherein:
a center point of the inlet port is offset from a center point of the discharge port by a distance such that the rotor cannot open both the inlet port and discharge port at the same time,
each of the three apexes is disposed between adjacent lobes of the three lobes such that the adjacent lobes of the three lobes share a common apex,
each of the three lobes extends between two of the three apexes,
each of the three lobes comprises two distinct arcs,
a first portion of each arc adjacent to one of the three apexes defining a non-smooth curve having a curvature that varies along a length thereof,
the curvature of the non-smooth curve is adapted to create a seal between an outer surface of the rotor and the peripheral wall of the rotor housing, and
the curvature of the non-smooth curve comprises two arcuate portions with different radii of curvature, such that an unwanted transfer of fluid is prevented;
wherein the rotor is fabricated of a flexible material so that the three apexes do not require separate sealing members; and
wherein the pump, during medicament delivery, is connectable to a motor, wherein medicament is drawn from the reservoir into the pump chamber in the rotor housing through the inlet as the rotor turns relative to the rotor housing and the medicament is expelled through the outlet and into the discharge device.

2. The medicament delivery device of claim 1 wherein the pump chamber comprises a first and second chamber.

3. The medicament delivery device of claim 1, further comprising:
a back plate having an inner surface, the rotor housing being positioned adjacent to the back plate;
a front plate support connected to the back plate;
a planetary gear transmission; and
an eccentric shaft operatively connected to the planetary gear transmission, the rotor being rotationally fixed to the eccentric shaft, wherein the planetary gear transmission comprises:
a stationary timing pinion positioned on the back plate; and
a ring gear integral with the rotor, wherein the ring gear has teeth that mesh with cooperating teeth on the timing pinion such that the ring gear rotates eccentrically around the timing pinion.

4. The medicament delivery device of claim 1 wherein the inlet port and the discharge port each have a longitudinal axis, wherein the longitudinal axis of the inlet port is parallel to and offset from the longitudinal axis of the discharge port.

5. The medicament delivery device of claim 1, further comprising:
a back plate having an inner surface, the rotor housing being positioned adjacent to the back plate; and
an eccentric shaft, the rotor being rotationally fixed to the eccentric shaft, wherein the eccentric shaft is connected to a drive shaft that is journaled to a bearing positioned in the back plate.

6. The medicament delivery device of claim 1 wherein the flexible material is silicone.

7. The medicament delivery device of claim 1, further comprising:
a back plate having an inner surface, the rotor housing being positioned adjacent to the back plate; and
a front plate support connected to the back plate, wherein the front plate support comprises both open areas and solid support areas.

8. The medicament delivery device of claim 1 wherein:
the inlet port is a first inlet port and the discharge port is a first discharge port,
the rotor housing further comprises a first chamber and a second chamber,
the first chamber has the first inlet port and the first discharge port, and the second chamber has a second inlet port and a second discharge port
each of the first and second inlet ports and the first and second discharge ports has a longitudinal axis, and
the first inlet port is positioned such that the longitudinal axis thereof is parallel to and offset from the longitudinal axis of the first discharge port, and the second inlet port is positioned such that the longitudinal axis thereof is parallel to and offset from the longitudinal axis of the second discharge port.

9. The medicament delivery device of claim 1, wherein the reservoir of medicament stores liquid medicament.

10. A medicament delivery device comprising:
a pump and a motor, the pump having an inlet connected to a reservoir of medicament and an outlet connected to a discharge device, the pump comprising:
a rotor housing having a peripheral wall, an inlet port, and a discharge port, wherein the peripheral wall defines a pump chamber with a trochoidal wall; and
a rotor movably positioned within the rotor housing, the rotor comprising three lobes and three respective apexes, wherein:
a center point of the inlet port is offset from a center point of the discharge port by a distance such that the rotor cannot open both the inlet port and discharge port at the same time,
each of the three apexes is disposed between adjacent lobes of the three lobes such that the adjacent lobes of the three lobes share a common apex,
each of the three lobes extends between two of the three apexes,
each of the three lobes comprises two distinct arcs,
a first portion of each arc adjacent to one of the three apexes defining a non-smooth curve having a curvature that varies along a length thereof,
the curvature of the non-smooth curve is adapted to create a seal between an outer surface of the rotor and the peripheral wall of the rotor housing, and
the curvature of the non-smooth curve comprises two arcuate portions with different radii of curvature, such that an unwanted transfer of fluid is prevented;
wherein the rotor is fabricated of a flexible material so that the three apexes do not require separate sealing members;

wherein the motor is connected to the pump during medicament delivery, wherein medicament is drawn from the reservoir into the pump chamber in the rotor housing through the inlet as the rotor turns relative to the rotor housing and the medicament is expelled through the outlet and into the discharge device.

11. The medicament delivery device of claim 10, wherein the pump is configured for the delivery of liquid medicament.

\* \* \* \* \*